United States Patent [19]

Lafon

[11] Patent Number: 4,713,395
[45] Date of Patent: Dec. 15, 1987

[54] ACETOHYDROXAMIC ACID DERIVATIVE

[75] Inventor: Louis Lafon, Paris, France

[73] Assignee: Societe Anonyme Dite: Laboratoire L. LaFon, Maisons Alfort, France

[21] Appl. No.: 890,561

[22] Filed: Jul. 30, 1986

[30] Foreign Application Priority Data

Jul. 31, 1985 [FR] France ................................ 85 11685

[51] Int. Cl.$^4$ ................... A61K 31/04; A61K 31/085; A61K 31/185; C07C 83/10
[52] U.S. Cl. ............................... 514/575; 260/500.5 H
[58] Field of Search ................. 260/500.5 H; 514/575

[56] References Cited

U.S. PATENT DOCUMENTS 3,787,569  1/1974  Johnson et al. ...................... 514/575
4,083,996  4/1978  Tanaka et al. ....................... 514/575

Primary Examiner—J. E. Evans
Attorney, Agent, or Firm—Wegner & Bretschneider

[57] ABSTRACT

The present invention relates, by way of a new industrial product, to an acetohydroxamic acid derivative, namely 2-(5-chloro-4-nitro-2-methoxybenzamido)acetohydroxamic acid.

This product is useful in therapy, in particular as a sedative.

It can be prepared by reacting NH$_2$OH with a C$_1$–C$_3$ lower alkyl 5-chloro-4-nitro-2-methoxybenzamidoacetate.

3 Claims, No Drawings

ACETOHYDROXAMIC ACID DERIVATIVE

The present invention relates, by way of a new industrial product, to an acetohydroxamic acid derivative, namely 2-(5-chloro-4-nitro-2-methoxybenzamido)acetohydroxamic acid. It also relates to the method for its preparation and its use in therapy, in particular as a sedative.

Patent Document BE-A-No. 852 738 has disclosed 2-(4-aminobenzamido)acetohydroxamic acid hydrochloride, which has the Code no.: CRL 40 473 and has effects on the central nervous system (see Example 18 of the said Belgian patent). 3-(3-Aminobenzamido)propionohydroxamic acid hydrochloride, which has the Code no.: CRL 40 816 and has particularly valuable antidepressant properties, is also known.

It has now been found, surprisingly, that the new compound according to the invention, namely 2-(5-chloro-4-nitro-2-methoxybenzamido)acetohydroxamic acid (Code no.: CRL 40 636), which is structurally different from the known products mentioned above, is particularly valuable in therapy on account of its effects on the central nervous system (CNS).

Briefly, CRL 40 636 according to the invention is noteworthy for its sedative effects, whereas (i) CRL 40 473 has moderate sedative and antidepressant effects and (ii) CRL 40 816 is more an antidepressant than a sedative.

The results of comparative tests recorded in Table I below show that CRL 40 636 (product of Example 1 according to the invention) is more active and acts at lower doses than CRL 40 473 (comparison product CP-1) and CRL 40 816 (comparison product CP-2) mentioned above, according to the so-called intergroup aggressiveness test.

A therapeutic composition recommended according to the invention contains, in association with a physiologically acceptable excipient, 2-(5-chloro-4-nitro-2-methoxybenzamido)acetohydroxamic acid of the structural formula:

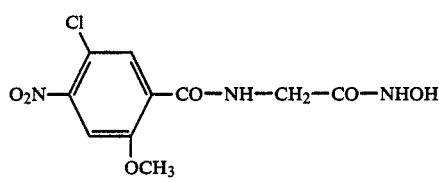

(I)

The compound according to the invention can be prepared using a method known per se by the application of conventional reaction mechanisms. The method recommended here consists in reacting hydroxylamine with a $C_1$-$C_3$ lower alkyl 5-chloro-4-nitro-2-methoxybenzamidoacetate at room temperature (15°-20° C.) for at least 1 hour, preferably for at least 4 hours, in proportions of 1 to 1.1 mol of $NH_2OH$ per mol of alkyl 5-chloro-4-nitro-2-methoxybenzamidoacetate.

The total synthesis of the product of the invention, starting from 5-nitro-4-chloro-2-methylaniline, is illustrated by diagram A below.

DIAGRAM A

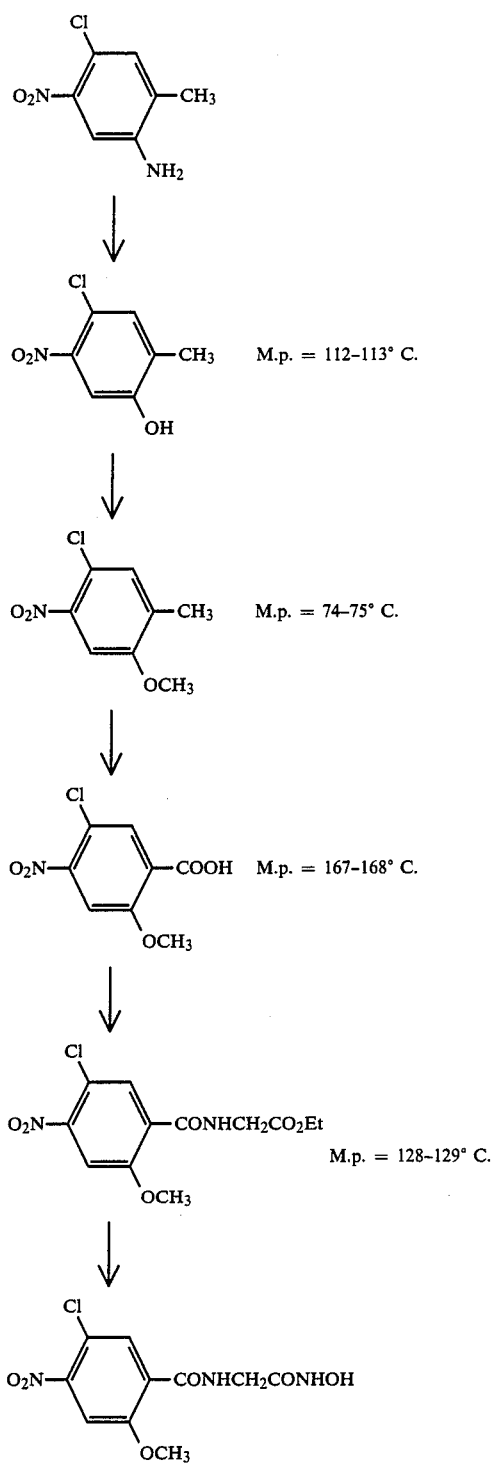

Further advantages and characteristics of the invention will be understood more clearly from the following description of a preparative example on the one hand and results of neuropsychopharmacological tests on the other. Of course, these data as a whole do not in any way imply a limitation but are given by way of illustration.

EXAMPLE 1

Preparation of 2-(5-chloro-4-nitro-2-methoxybenzamido)acetohydroxamic acid (Code no.: CRL 40 636)

A solution of hydroxylamine is prepared with 5.6 g (0.08 mol) of hydroxylamine hydrochloride and 3.68 g (0.16 g at) of sodium in 250 ml of methanol. 23.8 g (0.075 mol) of ethyl 5-chloro-4-nitro-2-methoxybenzamidoacetate are added and the ingredients are left in contact overnight. The sodium salt is filtered off, washed with methanol and dried. The dried product thus obtained is taken up in 200 ml of water, the mixture is filtered and the filtrate is precipitated with 3N HCl. The precipitate is filtered off, washed with water and dried. Recrystallization from a $C_2H_5OH/H_2O$ mixture (96:4 by weight) gives CRL 40 636 with a yield of 44%. M.p.=196°-198° C. (with decomposition).

The results of the tests which were undertaken with the compound according to the invention have been summarized below. In the present neuropsychopharmacological study, a suspension of CRL 40 636 in an aqueous solution of gum arabic was administered intraperitoneally in a volume of 20 ml/kg to male mice and 5 ml/kg to male rats.

I. TOXICITY

CRL 40 636 is not toxic. In fact, in mice, the $LD_0$ (maximum non-lethal dose) by intraperitoneal administration is greater than 1024 mg/kg.

II. OVERALL BEHAVIOR AND REACTIVITIES

Groups of three animals are observed before and then 0.25 hour, 0.50 hour, 1 hour, 2 hours, 3 hours and 24 hours after the administration of CRL 40 636. The following observations are made:

(1°) in mice at a dose of 512 mg/kg:
  sedation with a decrease in the fear and aggressiveness reactions, the muscular strength and the reactivity to touch for 3 hours,
  hypothermia (−6.8° C.) for more than 3 hours, and
  depressed respiration for 2 to 3 hours;
at a dose of 128 mg/kg:
  sedation with a decrease in the fear and aggressiveness reaction for 3 hours,
  hypothermia (−3.1° C.) for 2 hours, and
  depressed respiration for 2 to 3 hours;
at a dose of 32 mg/kg:
  sedation (2 out of 3 animals) for 3 hours,
  moderate hypothermia (−2.2° C.) for 1 hour, and
  depressed respiration (2 out of 3 animals) for 2 hours; and
at a dose of 8 mg/kg:
  variable sedation (2 out of 3 animals) for 0.5 to 1 hour; and (2°) in rats at a dose of 256 mg/kg:
  sedation for 24 hours with a decrease in the muscular strength and tonus for 1 to 3 hours,
  mydriasis for 2 hours, and
  depressed respiration for 1 to 3 hours;
at a dose of 64 mg/kg:
  sedation for 1 to 3 hours with a decrease in the muscular strength and tonus, and
  depressed respiration for 1 hour;
at a dose of 16 mg/kg:
  sedation (0.25 to 1 hour) with a decrease in the muscular strength and tonus, and
  depressed respiration for 0.25 to 1 hour; and
at a dose of 4 mg/kg:
  sedation for 0.25 to 0.50 hour accompanied by muscular hypotonia, and
  depressed respiration for 0.25 hour.

III. INTERACTION WITH APOMORPHINE (1°) In mice

Half an hour after the administration of CRL 40 636, groups of 6 mice receive a subcutaneous injection of apomorphine at a dose of 1 or 16 mg/kg. It is found that, at doses of 128 and 512 mg/kg, CRL 40 636 (which exerts a significant hypothermic effect when administered by itself) does not oppose the hypothermia, the righting attitude or the stereotypies induced by apomorphine in mice.

(2°) In rats

Apomorphine is injected subcutaneously at a dose of 0.5 mg/kg into groups of 6 rats 0.5 hour after the administration of CRL 40 636. It is observed that the stereotypies induced by apomorphine in rats are not modified by CRL 40 636.

IV. INTERACTION WITH AMPHETAMINE 0.5 hour or 1 hour after the administration of CRL 40 636, groups of 6 rats receive an intraperitoneal injection of 2 mg/kg of amphetamine.

It is found that, as from a dose of 4 mg/kg, CRL 40 636 strongly antagonizes the stereotypies induced by amphetamine (whereas CRL 40 816, mentioned above, only causes a moderate decrease in the said stereotypies as from a dose of 256 mg/kg i.p.); it is also observed that, although the antagonism of these stereotypies by CRL 40 636 is very intense initially, it seems to disappear rapidly.

V. INTERACTION WITH RESERPINE

Four hours after the administration of reserpine (2.5 mg/kg), groups of 6 mice receive CRL 40 636. It is found that CRL 40 636 does not modify the hypothermia or the ptosis induced by reserpine.

VI. INTERACTION WITH OXOTREMORINE

Oxotremorine (0.5 mg/kg) is injected intraperitoneally into groups of 6 mice half an hour after the administration of CRL 40 636. It is observed that CRL 40 636, which exerts a significant hypothermic effect at doses of 32, 128 and 512 mg/kg, does not oppose, at these doses, the hypothermia induced by oxotremorine, that it is devoid of any effect on the trembling caused by oxotremorine, but that it seems to prolong lachrymation (implying an action on the peripheral cholinergic symptoms).

VII. ACTION ON THE FOUR PLATE TEST, TRACTION AND ELECTRIC SHOCK

The test is performed on groups of 10 mice half an hour after the administration of CRL 40 636. It is found that CRL 40 636 does not cause an increase in the number of punished passes, that, at a high dose, it causes motor incapacity in 30% of the animals, and that it does not modify the convulsant and lethal effects of electric shock.

VIII. ACTION ON THE SPONTANEOUS MOTILITY

Half an hour after they have received CRL 40 636, the mice (6 per dose, 12 control animals) are placed in an actimeter, where their motility is recorded for 0.5 hour. It is found that, at doses of 128 and 512 mg/kg, CRL 40 636 causes a significant decrease in the spontaneous motility, whereas CRL 40 816, mentioned above, only causes a moderate decrease in the said motility at a dose of 512 mg/kg.

IX. ACTION ON THE INTERGROUP AGGRESSIVENESS (comparative study)

After they have stayed for 3 weeks in the two halves of a cage divided by an opaque partition, groups of 3 male mice (each mouse weighing about 20 g) receive the products to be tested, namely CRL 40 636 (Example 1), CRL 40 473 (CP-1) and CRL 40 816 (CP-2), by intraperitoneal administration in an aqueous solution of gum arabic, at a rate of three cages per product and per dose and six cages for the control animals receiving only the aqueous solution of gum arabic by intraperitoneal administration. Half an hour later, the two groups from the same cage are brought together and the number of fights which occur in 10 minutes is noted. The results are collated in Table I below and show that CRL 40 636 according to the invention (i) greatly decreases the number of fights at a dose of 64 mg/kg, (ii) totally eliminates fights at a dose of 128 mg/kg, and (iii) has a beneficial antiaggressive effect which is considerably greater than that of CRL 40 473 according to Example 18 of the abovementioned Belgian patent, on the one hand, and that of CRL 40 816, on the other.

TABLE I

Comparative tests

| Product | Code No. | Dose (mg/kg) | Number of fights per mouse | Decrease in the number of fights compared with the control animals |
|---|---|---|---|---|
| control animals | — | — | 3.05 | 0% |
| Ex. 1 | CRL 40 636 | 64 | 1.48 | 51% |
| Ex. 1 | CRL 40 636 | 128 | 0 | 100% |
| CP-1 | CRL 40 473 | 128 | 1.80 | 40% |
| CP-1 | CRL 40 473 | 512 | 2.23 | 26% |
| CP-2 | CRL 40 816 | 128 | 1.42 | 53% |
| CP-2 | CRL 40 816 | 512 | 0 | 100% |

Note:
structural formulae of the products

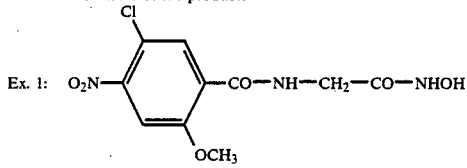

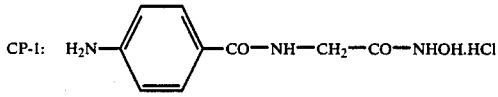

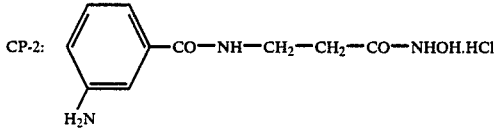

X. ACTION TOWARDS SOME FORMS OF BEHAVIOR PERTURBED BY VARIOUS AGENTS (1°) Motility reduced by habituation to the enclosure After they have stayed in the actimeters for 18 hours, the mice (6 per dose, 12 control animals) receive CRL 40 636. They are immediately returned to their respective enclosures and, half an hour later, their motility is recorded for 30 minutes.

It is observed that CRL 40 636 does not cause a distinct resumption in the motor activity of mice accustomed to their enclosure.

(2°) Motility reduced by hypoxic aggression

Half an hour after they have received CRL 40 636, the mice (10 per dose, 20 control animals) are subjected to acute hypobaric anoxia [pressure reduction of 600 mm Hg (i.e. about $8 \times 10^4$ Pa) in 90 seconds; release of vacuum in 45 seconds] and are then placed in an actimeter, where their motility is recorded for 10 minutes.

It is observed that CRL 40 636 does not cause a distinct improvement in the motor recovery of mice whose motility has been depressed following a brief period in a reduced-pressure enclosure.

(3°) Asphyxiant anoxia

Groups of 10 mice receive CRL 40 636 half an hour before the intraperitoneal administration of 32 mg/kg of gallamine triiodoethylate (reference curarizing agent).

It is observed that CRL 40 636 does not modify the time taken for convulsions and death to occur following asphyxiant anoxia caused by a curarizing agent.

XI. COMPLEMENTARY TEST

A complementary test was performed with the product according to the invention, the latter being administered gastrically, as a suspension in an aqueous solution of gum arabic, in a volume of 5 ml/kg, to groups of 6 male rats 0.5 hour or 1 hour before the intraperitoneal administration of 2 mg/kg of amphetamine.

It is found that CRL 40 636 briefly antagonizes the stereotypies induced by amphetamine in rats.

XII. CONCLUSIONS

The results of the tests given above show that CRL 40 636 exhibits, in its neuropsychopharmacological profile, very intense, essentially sedative effects demonstrated by hypomotility, hypothermia, a decrease in the reactivities and a decrease in the intergroup aggressiveness, and that it is practically devoid of antidepressant effects (no antagonism of the hypothermia induced by apomorphine, reserpine and oxotremorine).

In clinical trials on adult humans, CRL 40 636 was shown to be an excellent sedative when administered orally at a daily dose of 50 to 100 mg. The dosage to be administered consists especially of two to four tablets or gelatine capsules per day, each containing 25 mg of CRL 40 636.

The use of 2-(5-chloro-4-nitro-2-methoxybenzamido)acetohydroxamic acid is recommended for obtaining a sedative drug intended for therapeutic purposes in patients requiring a drug of this kind, especially in cases of overexcitement.

What is claimed is:

1. 2-(5-Chloro-4-nitro-2-methoxybenzamido)acetohydroxamic acid.

2. A therapeutic composition comprising, in association with a physiologically acceptable excipient, a pharmaceutically effective amount of 2-(5-chloro-4-nitro-2-methoxybenzamido)acetohydroxamic acid according to claim 1.

3. A method for treating a patient suffering from overexcitement, which comprises administering to such a patient a pharmaceutically effective amount of 2-(5-chloro-4-nitro-2-methoxybenzamido)acetohydroxamic acid according to claim 1.

* * * * *